United States Patent
Floyd, III et al.

(10) Patent No.: US 10,207,001 B2
(45) Date of Patent: Feb. 19, 2019

(54) TECHNIQUES FOR RELEASE OF MATERIAL INTO AN ENVIRONMENT

(71) Applicant: LAWRENCE LIVERMORE NATIONAL SECURITY, LLC, Livermore, CA (US)

(72) Inventors: William C. Floyd, III, Oakland, CA (US); Roger D. Aines, Livermore, CA (US); Eric B. Duoss, Dublin, CA (US); John J. Vericella, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 25 days.

(21) Appl. No.: 15/010,066

(22) Filed: Jan. 29, 2016

(65) Prior Publication Data

US 2016/0144030 A1    May 26, 2016

Related U.S. Application Data

(62) Division of application No. 14/061,589, filed on Oct. 23, 2013.

(51) Int. Cl.
| | |
|---|---|
| *F42B 5/08* | (2006.01) |
| *A61K 41/00* | (2006.01) |
| *F42B 14/00* | (2006.01) |
| *A61N 5/06* | (2006.01) |
| *A61K 9/48* | (2006.01) |
| *C06B 45/00* | (2006.01) |
| *G01N 33/24* | (2006.01) |
| *A61K 47/32* | (2006.01) |

(52) U.S. Cl.
CPC ........ *A61K 41/0028* (2013.01); *A61K 9/4816* (2013.01); *A61K 9/4841* (2013.01); *A61K 47/32* (2013.01); *A61N 5/06* (2013.01); *A61N 5/062* (2013.01); *C06B 45/00* (2013.01); *F42B 5/08* (2013.01); *F42B 14/00* (2013.01); *G01N 33/24* (2013.01)

(58) Field of Classification Search
CPC .... C06B 23/00; F42B 5/08; F42B 5/38; F42B 14/00
USPC .............................. 149/2; 102/334, 336, 342
See application file for complete search history.

(56) References Cited

U.S. PATENT DOCUMENTS

| | | |
|---|---|---|
| 2012/0214219 A1 | 8/2012 | Aines et al. |
| 2013/0017610 A1 | 1/2013 | Roberts |

FOREIGN PATENT DOCUMENTS

| | | |
|---|---|---|
| EP | 0102450 | 3/1984 |
| WO | 2010005847 | 1/2010 |

OTHER PUBLICATIONS

Nutley et al. (Occasional Paper No. 34, Aug. 2003, Center for Strategy and Technology) Non-Lethal Weapons: Setting Our Phasers on Stun?. . .*

(Continued)

*Primary Examiner* — Aileen B Felton
(74) *Attorney, Agent, or Firm* — Eddie E. Scott

(57) ABSTRACT

Systems and methods for releasing a material into an environment. The material may be encapsulated in a receptacle or otherwise packaged for movement into the environment. The receptacle with the material inside is introduced into the environment. A

(56) References Cited

OTHER PUBLICATIONS

Klinger et al., "Polymeric Photoresist Nanoparticles: Light-Induced Degradation of Hydrophobic Polymers in Aqueous Dispersion," Macromol. Rapid Comm., vol. 32, 2011, pp. 1979-1985.
International Search Report for PCT/US09/49415, 6 pages.

* cited by examiner

HEAT/ACID

HEAT/ACID

R=Me, Ph

HEAT/ACID

ACID

HEAT/ACID

HEAT/ACID

HEAT/ACID

HEAT/ACID

HEAT/ACID

HEAT/ACID

R= Me, Ph

HEAT/ACID

HEAT/STRONG NUCLEOPHILES

STRONG/
NUCLEOPHILES

HYPOXIA

HEAT + ACID /
STRONG ACID

ULTRA VIOLET/
INFRA RED

ULTRA VIOLET

ULTRA VIOLET/
INFRA RED (NOVOLAKS)

HEAT / ACID

HEAT / ACID

TECHNIQUES FOR RELEASE OF MATERIAL INTO AN ENVIRONMENT

CROSS-REFERENCE TO RELATED APPLICATIONS

The present application is a Division of application Ser. No. 14/061,589 filed Oct. 23, 2013, entitled "Techniques for Release of Material into an Environment", the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to material release and more particularly to techniques for material release.

State of Technology

Chemically amplified photoresists have been previously used to selectively alter the solubility properties and chemical makeup of polymeric materials with high spacial resolution in the photoresist industry. This technology uses a light or heat activated acid or base catalyst impregnated in a polymer matrix. Upon activation by light or heat, this catalyst induces a chemical change in the polymer surrounding it, resulting in increased solubility in the surrounding environment, polymer degradation, etc.

In oil and gas wells, a tracer agent such as fluorescein is injected into wells to monitor material flow below the surface. While appearance of this tracer in other wells may give indications regarding flow direction, it does not yield any valuable thermal information regarding the environments below. It would be useful to encapsulate the tracer agent in a thermally responsive shell, which would serve to indicate the temperatures present in the relevant well spaces.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

In various embodiments, the present invention provides systems and methods for releasing a material into an environment. The material may be encapsulated in a receptacle or otherwise packaged for movement into the environment. The receptacle with the material inside is introduced into the environment. A triggering causes release of the material from the receptacle into the environment. In various other embodiments, the present invention provides a method of releasing a material into an environment. In one embodiment a material and a catalyst are encapsulated in a receptacle. Activation of the catalyst is triggered to act on the material. The receptacle with the activated material is introduced into the environment. A triggering causes release of the activated material from the receptacle into the environment.

The present invention has many uses. For example, the present invention has use in geological applications, in the release of drugs and therapeutics in biological and medical applications, and in the delivery of other useful encapsulated materials where non-encapsulated delivery seems untenable.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
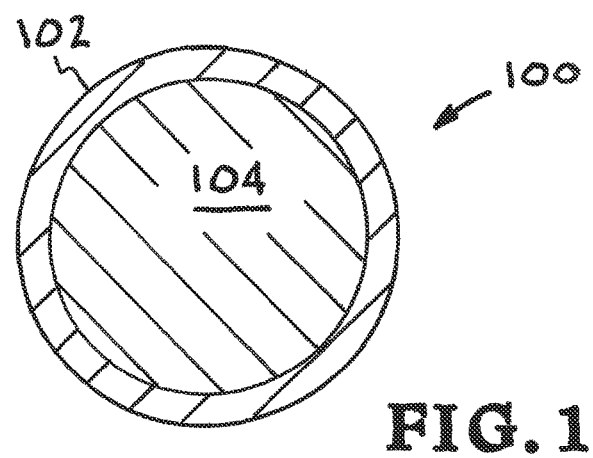
FIG. 1 illustrates an individual receptacle.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention allows for the release of encapsulated contents in an efficient manner under predetermined conditions and environments. The invention allows for release of crosslinking and reporting agents in geological applications, release of drugs and therapeutics in biological and medical applications, and delivery of other useful encapsulated materials where nonencapsulated delivery seems untenable.

The present invention provides triggerable receptacles and their use release of the encapsulated contents. This allows for an external trigger (including temperature, uv light, IR light, and chemical reagents) to activate release (including acids, bases, and other highly reactive species) which causes a highly amplified change to the encapsulating material (including removal of hydrophobic or hydrophilic groups, cleaving of chemical bonds, degradation of cross-linking bonds, or other chemical rearrangements resulting in a marked difference in chemical reactivity) which in turn results in a change in the physical properties of the shell (including dissolving, decomposition, combustion, and swelling). This process results in an ability to achieve an efficient catalytic encapsulant degradation or alternate response from a chosen triggering mechanism.

Referring now to the drawings, in various embodiments the present invention provides release of encapsulated contents in an efficient manner under predetermined conditions and environments. In various embodiments, the present invention provides release of a material into an environment. The material is encapsulated in a receptacle. The receptacle with the material inside is introduced into the environment. A triggering causes release of the material from the receptacle into the environment.

Referring now to FIG. 1, an individual receptacle is illustrated. The individual receptacle is designated generally by the reference numeral 100. The receptacle 100 provides a mechanism for releasing a material into the environment. The receptacle 100 includes an outer shell or skin 102. A material 104 is encapsulated within the outer shell or skin 102 of the receptacle 100. The receptacle 100 with the material 104 inside is introduced into the environment. A triggering causes release of the material 104 from the receptacle 100 into the environment.

In one embodiment, the outer shell or skin 102 of the receptacle 100 is a polymer coating that forms the outer shell or skin 102. The active materials 104 are encapsulated within the polymer coating 102. The polymer surface layer 102 can be made of any of several families of polymers, including polystyrene, polyethylene, polypropylene, nylon, and others. The active materials 104 encapsulated within the capsule 100 can be pure material or a mixture of materials. For example, the polymer coating 102 can be used to encapsulate solid materials 104 that would ordinarily require special handling, or be unavailable for applications where their reactivity without encapsulation prohibits transport to the point of use.

Figure 2:
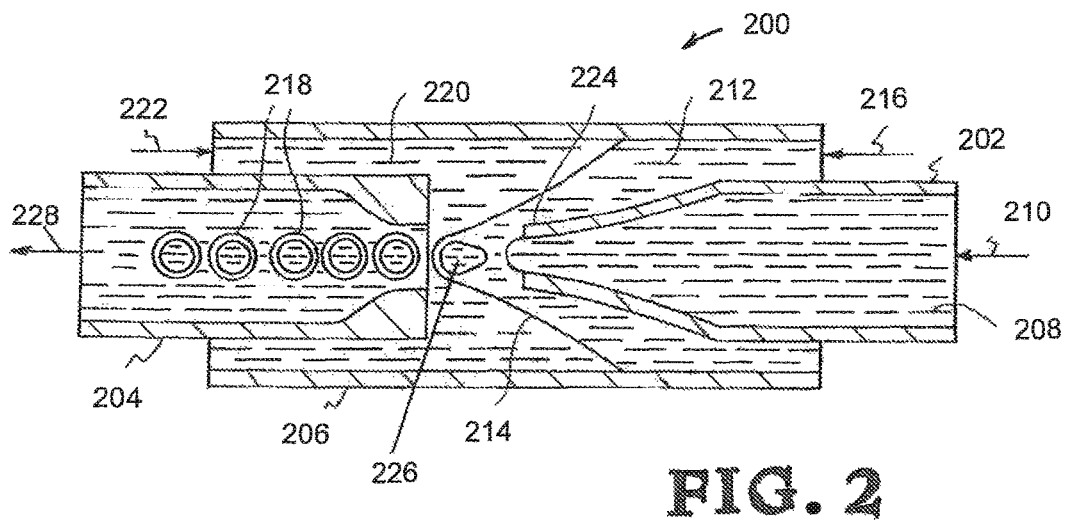
FIG. 2 illustrates a system that can be used for making a capsule.

Referring now FIG. 2, a system is illustrated that can be used for making the capsule 100 shown in FIG. 1. FIG. 2 illustrates one embodiment of a system and method of fabricating capsules containing materials. The present invention provides encapsulation of materials for subsequent release into the environment. The system is designated generally by the reference numeral 200. The system 200 has use where it is important to control reactivity, size distribution, surface area, and to be able to trigger release via a triggering event. The system 200 provides enhanced transport through the polymer shell (e.g. bursting of the shell, or an increase in permeability due to temperature). The system 200 can be used to encapsulate solid materials that would ordinarily require special handling, or be unavailable for applications where their reactivity without encapsulation prohibits transport to the point of use.

The system 200 for making capsules containing materials is schematically illustrated in FIG. 2. The system is designated generally by the reference numeral 200. The system 200 includes the following items:

an injection tube 202,
a collection tube 204,
an outer tube 206,
inner fluid containing the material 208,
middle fluid polymer encapsulation material 212,
boundary layer 214,
microcapsules 218,
outer fluid 220,
droplet forming nozzle 224, and
droplets containing the materials 226.

The structural element of the system 200 having been described, the operation of the system 200 will now be considered. The inner fluid of materials 208 is flowing in the direction indicated by arrow 210 into the droplet forming nozzle 224. The middle fluid 212 flows in the outer tube 206 in the direction indicated by arrow 216. The droplets of materials 226 become encased in the middle fluid 212 forming microcapsules 218 that have the material contained in an outer shell of the middle fluid 212. The outer fluid 220 flows in the outer tube 206 in the direction indicated by arrow 222. The outer fluid 220 helps form the boundary layer 214 and also flows through the collection tube 204. This outer fluid 220 carries the fabricated microcapsules 218 through the collection tube 204 as indicated by the arrow 228. The boundary layer 224 between the middle fluid 214 and the outer fluid 220 helps direct the droplets of materials 226 into the collection tube 204 and helps produce the outer shell.

Systems for producing microcapsules are described in U.S. Pat. No. 7,776,927 and in U.S. Published Patent Application Nos. 2009/0012187 and 2009/0131543. U.S. Pat. No. 7,776,927 to Liang-Yin Chu et al, assigned to the President and Fellows of Harvard College, discloses emulsions and the production of emulsions, including multiple emulsions and microfluidic systems for producing multiple emulsions. A multiple emulsion generally describes larger droplets that contain one or more smaller droplets therein which, in some cases, can contain even smaller droplets therein, etc. Emulsions, including multiple emulsions, can be formed in certain embodiments with generally precise repeatability, and can be tailored to include any number of inner droplets, in any desired nesting arrangement, within a single outer droplet. In addition, in some aspects of the invention, one or more droplets may be controllably released from a surrounding droplet. U.S. Published Patent Application No. 2009/0012187 to Liang-Yin Chu et al, assigned to the President and Fellows of Harvard College, discloses multiple emulsions, and to methods and apparatuses for making emulsions, and techniques for using the same. A multiple emulsion generally describes larger droplets that contain one or more smaller droplets therein which, in some cases, can contain even smaller droplets therein, etc. Emulsions, including multiple emulsions, can be formed in certain embodiments with generally precise repeatability, and can be tailored to include any number of inner droplets, in any desired nesting arrangement, within a single outer droplet. In addition, in some aspects of the invention, one or more droplets may be controllably released from a surrounding droplet. U.S. Published Patent Application No. 2009/0131543 to David A. Weitz discloses multiple emulsions, and to methods and apparatuses for making multiple emulsions. A multiple emulsion, as used herein, describes larger droplets that contain one or more smaller droplets therein. The larger droplet or droplets may be suspended in a third fluid in some cases. In certain embodiments, emulsion degrees of nesting within the multiple emulsions are possible. For example, an emulsion may contain droplets containing smaller droplets therein, where at least some of the smaller droplets contain even smaller droplets therein, etc. Multiple emulsions can be useful for encapsulating species such as pharmaceutical agents, cells, chemicals, or the like. In some cases, one or more of the droplets (e.g., an inner droplet and/or an outer droplet) can change form, for instance, to become solidified to form a microcapsule, a lipo some, a polymero some, or a colloidosome. As described below, multiple emulsions can be formed in one step in certain embodiments, with generally precise repeatability, and can be tailored to include one, two, three, or more inner droplets within a single outer droplet (which droplets may all be nested in some cases). As used herein, the term "fluid" generally means a material in a liquid or gaseous state. Fluids, however, may also contain solids, such as suspended or colloidal particles. U.S. Pat. No. 7,776,927 and U.S. Published Patent Application Nos. 2009/0012187 and 2009/0131543 are incorporated herein by this reference.

Figure 3A:
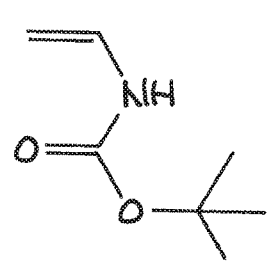
FIGS. 3A through 3T illustrate various chemical compounds that can be used to make capsule shells and their release into the environment.
Figure 3B:
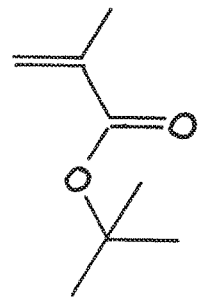
Figure 3C:
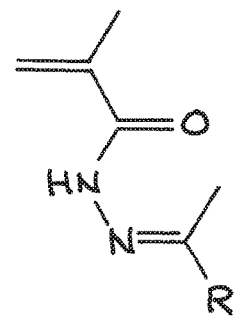
Figure 3D:
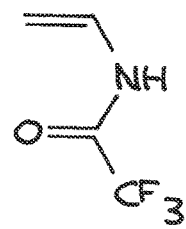
Figure 3E:
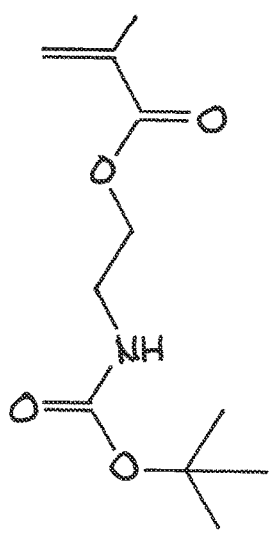
Figure 3F:
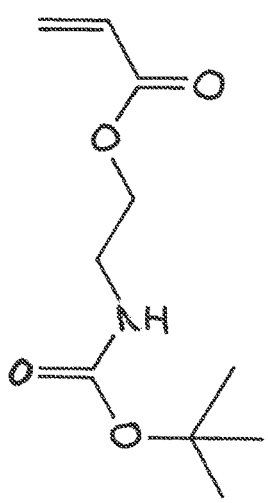
Figure 3G:
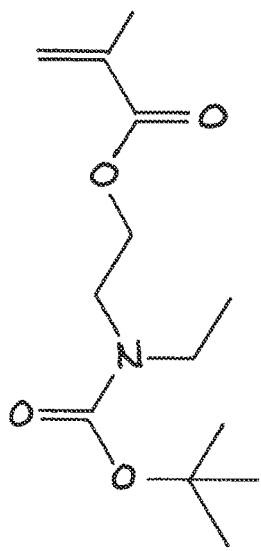
Figure 3H:
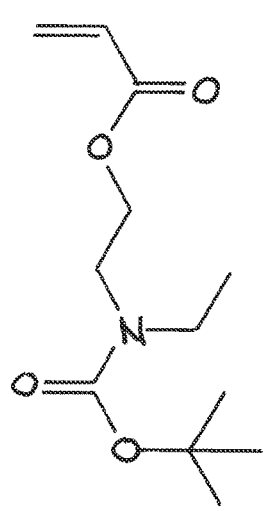
Figure 3I:
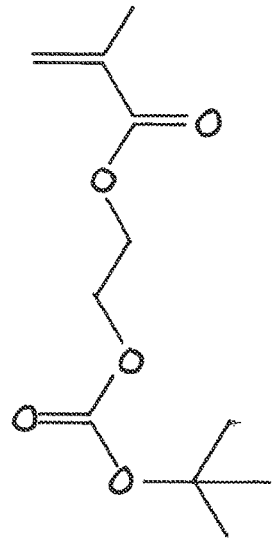
Figure 3J:
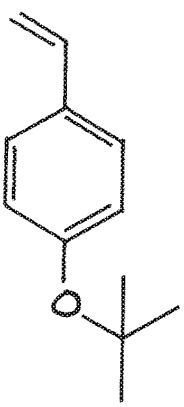
Figure 3K:
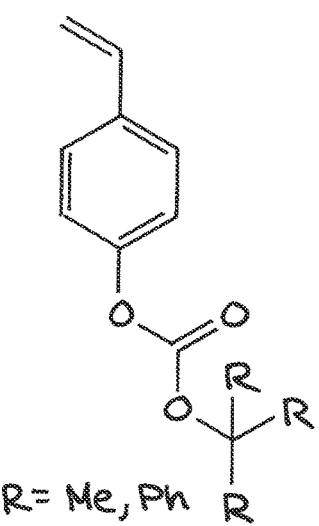
Figure 3L:
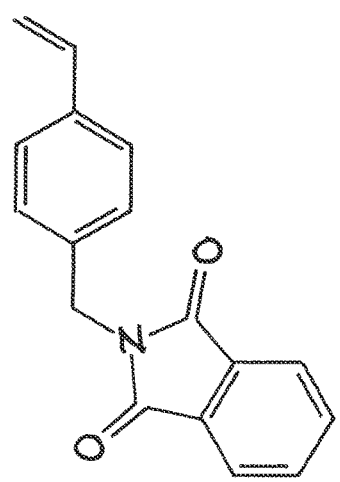
Figure 3M:
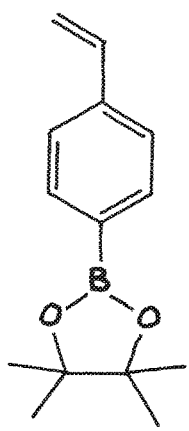
Figure 3N:
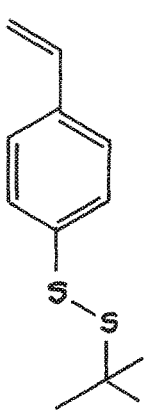
Figure 3O:
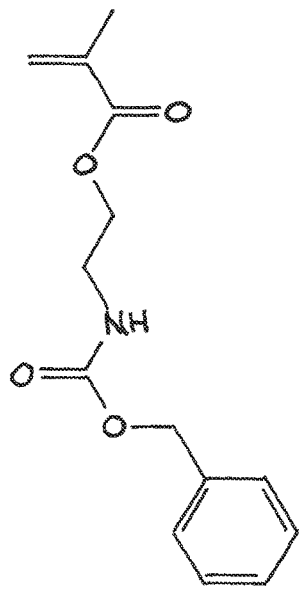
Figure 3P:
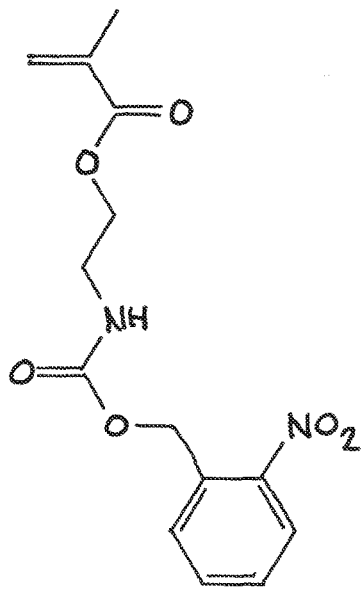
Figure 3Q:
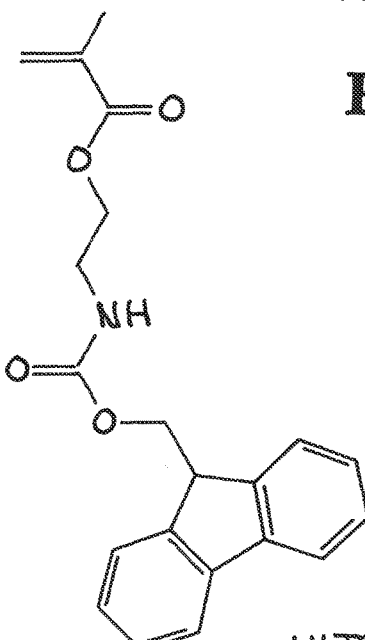
Figure 3R:
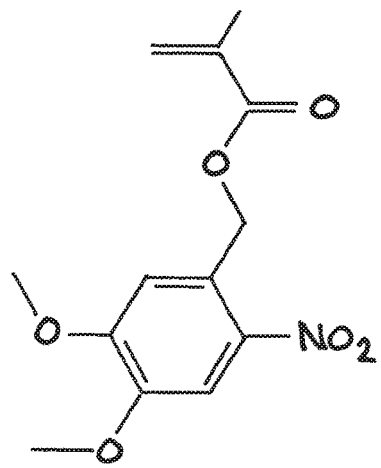
Figure 3S:
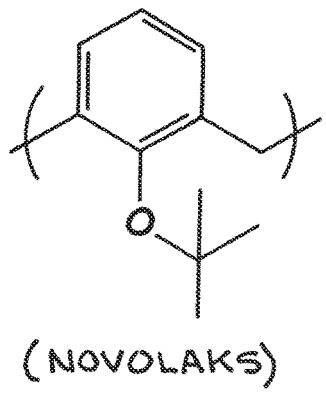
Figure 3T:
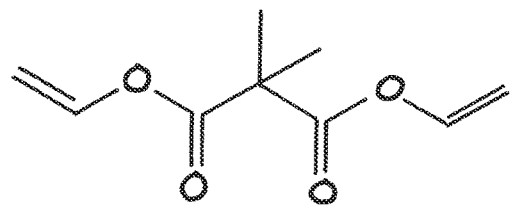

Referring now FIGS. 3A through 3T, various chemical compounds that can be used to make capsule shells and their release into the environment are illustrated. The trigger mechanisms are listed below the compound.

As illustrated in FIG. 3A, the compound Carbamic acid, N-ethenyl-, 1,1-dimethylethyl ester (or tert-butyl N-vinyl-carbamate) can be triggered by heat or acid. The material is released into a desired environment.

As illustrated in FIG. 3B, the compound tert-butyl methacrylate can be triggered by heat or acid. The material is released into a desired environment.

As illustrated in FIG. 3C, the compound 2-Propenoic acid, 2-methyl-, 2-(1-methylethylidene)hydrazide can be triggered by heat or acid. The material is released into a desired environment.

As illustrated in FIG. 3D, the compound trifluoroacetyl allyl amine is triggered by acid. The material is released into a desired environment.

As illustrated in FIG. 3E, the compound 2-Propenoic acid, 2-methyl-, 2-[[(1,1-dimethylethoxy)carbonyl]amino]ethyl ester can be triggered by heat or acid. The material is released into a desired environment.

As illustrated in FIG. 3F, the compound 2-Propenoic acid, 2-[[(1,1-dimethylethoxy)carbonyl]amino]ethyl ester can be triggered by heat or acid. The material is released into a desired environment.

As illustrated in FIG. 3G, the compound 2-((4,4-dimethylpent-1-en-2-yl)(ethyl)amino)ethyl methacrylate can be triggered by heat or acid. The material is released into a desired environment.

As illustrated in FIG. 3H, the compound 2-((4,4-dimethylpent-1-en-2-yl)(ethyl)amino)ethyl acrylate can be triggered by heat or acid. The material is released into a desired environment.

As illustrated in FIG. 3I, the compound 2-Propenoic acid, 2-methyl-, 2-[[(1,1-dimethylethoxy)carbonyl]oxy]ethyl ester can be triggered by heat or acid. The material is released into a desired environment.

As illustrated in FIG. 3J, the compound 1-tert-butoxy-4-vinylbenzene can be triggered by heat or acid. The material is released into a desired environment.

As illustrated in FIG. 3K, the compound tert-butyl 4-4vinylphenyl carbonate or trityl 4-vinylphenyl carbonate can be triggered by heat or acid. The material is released into a desired environment.

As illustrated in FIG. 3L, the compound 1H-Isoindole-1,3(2H)-dione, 2-[(4-ethenylphenyl)methyl]- can be triggered by heat or strong nucleophiles. The material is released into a desired environment.

As illustrated in FIG. 3M, the compound 1,3,2-Dioxaborolane, 2-(4-ethenylphenyl)-4,4,5,5-tetramethyl- can be triggered by heat or strong nucleophiles. The material is released into a desired environment.

As illustrated in FIG. 3N, the compound 1-(tert-butyl)-2-(4-vinylphenyl)disulfane is triggered by hypoxia. The material is released into a desired environment.

As illustrated in FIG. 3O, the compound 2-Propenoic acid, 2-methyl-, 2-[[(phenylmethoxy)carbonyl]amino]ethyl ester can be triggered by heat and acid or strong acid. The material is released into a desired environment.

As illustrated in FIG. 3P, the compound 2-((((2-nitrobenzyl)oxy)carbonyl)amino)ethyl methacrylate can be triggered by ultra violet or infra-red light. The material is released into a desired environment.

As illustrated in FIG. 3Q, the compound 2-(((((9H-fluoren-9-yl)oxy) carbonyl)amino)ethyl methacrylate can be triggered by ultra violet light or removed by a base. The material is released into a desired environment.

As illustrated in FIG. 3R, the compound 4,5-diethyl-2-nitrobenzyl methacrylate can be triggered by ultra violet or infra-red light. The material is released into a desired environment.

As illustrated in FIG. 3S, the compound novolac and other O-alkyl phenolic resins can be triggered by heat or acid. The material is released into a desired environment.

As illustrated in FIG. 3T, the compound divinyl 2,2-dimethylmalonate can be triggered by heat or acid. The material is released into a desired environment.

EXAMPLES

The present invention is further described and illustrated by a number of examples of systems constructed in accordance with the present invention. Various changes and modifications of these examples will be apparent to those skilled in the art from the description of the examples and by practice of the invention. The scope of the invention is not intended to be limited to the particular examples disclosed and the invention covers all modifications, equivalents, and alternatives falling within the spirit and scope of the invention as defined by the claims.

Example—Tracer for Interrogation of Potential Geothermal Formations

An example of an exploitable geothermal formation is an underground hydrothermal formation containing water with a suitable elevated temperature, usually between 40 and 120 degrees, and preferably between 70 and 90 degrees. Exploration for potential exploitable geothermal formation needs a simple, reliable, and cost effective way of determining whether suitable elevated temperatures exist within an underground reservoir.

This can be accomplished by the present invention wherein a capsule is injected into the underground formation. The capsule contains a tracer (for example a dye) and a trigger mechanism that is activated at a predetermined temperature. If the capsule encounters the predetermined temperature the trigger causes the tracer (dye) to be released and recovery of the released tracer (dye) indicates the underground formation has the suitable elevated temperature.

Referring again to FIG. 1, a tracer material 104 is encapsulated in a shell 102. The tracer material 104 can be a standard tracer material such as fluorescein disodium hydrate and 2,6-napthalein disulfonic acid sodium salt. The tracer is usually dissolved or suspended in an aqueous solution. The appearance of the tracer material in the recovered fluid can be measured using HPLC with a fluorescence detector.

The tracer material 104 is encapsulated in shell 102. The shell 102 can be made of different materials and different wall thicknesses to achieve the desired result. The shell 102 can be any number of polymer or other materials which are designed to dissolve, erode, or otherwise degrade under specific conditions such a predetermined temperature.

The shell materials are water soluble polymers modified with hydrophobic moieties that are degraded in the presence of heat, acid, or other relevant triggering events. These groups may be tertiary butyl carbonates or carbamates, substituted benzyl carbonates or carbamates, trityl groups, tertiary esters, or other groups designed to degrade at elevated temperature. The decomposition temperature of a given hydrophobic group can be varied by increasing or decreasing the stability of carbocations produced at elevated temperatures. For example, a tertiary butyl carbonate will produce a relatively stable tertiary carbocation upon heating, while a methyl carbonate will produce a relatively unstable methyl carbocation upon heating. The decomposition temperature of the tertiary butyl carbonate will therefore be lower. These trends of thermal stability can be used as a general guide for predicting the temperature at which the shell material will become soluble. For example, the tertiary butyl carbonate of poly (hydroxyethyl acrylate) will decompose at approximately 170-180° C., at which point the hydrophobic shell will be converted to hydrophilic poly (hydroxyethyl acrylate), as well as carbon dioxide and isobutylene resulting from the decomposition of the tertiary butyl carbonate. This evolution of carbon dioxide may also serve as a mechanism for inducing shell failure and release of capsule contents. For a higher decomposition temperature, a less substituted carbonate, for example an isopropyl carbonate, could be used. For a lower decomposition temperature, substituting a methyl group of the tertiary butyl carbonate with an electron donating phenyl ring will cause a more stable carbocation to be formed upon heating, which will lower the decomposition temperature. In the same manner, a trityl carbonate would have lower decomposition still.

An alternate route to lowering or modifying the decomposition temperature is to incorporate a thermal acid generator (TAG) into the shell or interior fluid of the capsule. At elevated temperature, these compounds induce an acidic environment, which will also cause the hydrophobic groups modifying the water soluble polymers to decompose, resulting in release of capsule contents. Because many of the chemical moieties sensitive to temperature are also sensitive to acidic environments, this is a way to induce a capsule to release its contents at the activation temperature of the TAG rather than the normal decomposition temperature of the hydrophobic group used to modify the shell polymer.

Figure 4:
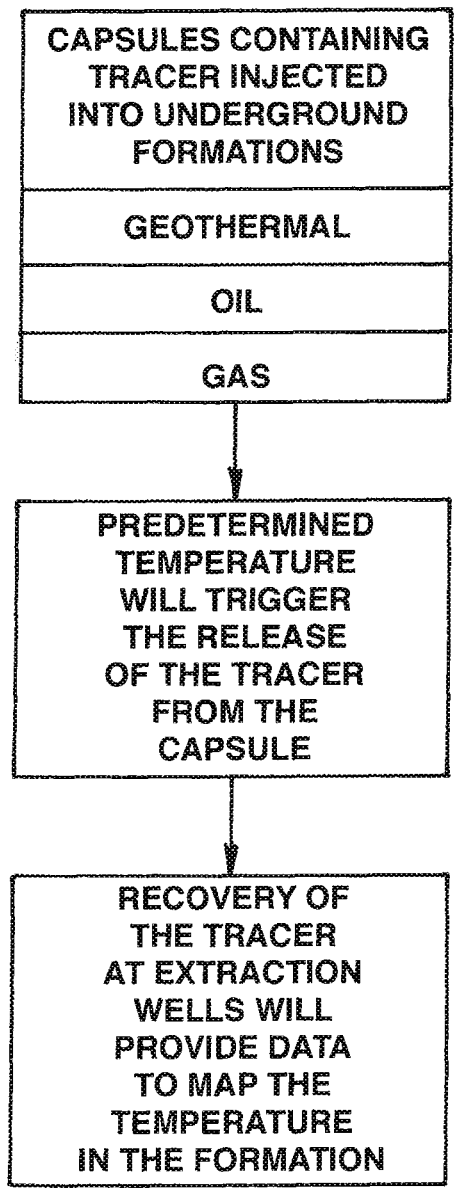
FIG. 4 is an illustration of one example of a system of the present invention.

Referring now to FIG. 4, the example of a tracer for interrogation of potential geothermal formations of the present invention is illustrated by a flow chart.

In the first step the capsule containing the tracer is injected into the underground formation.

In the next step the tracer is released from the capsule in the underground formation upon encountering the pre-determined temperature. The trigger mechanism is activated to act on the shell of the capsule to release the tracer into the underground formation.

In the final step the tracer is recovered. For example fluid may be recovered at an extraction well. If the tracer has been released by encountering the predetermined temperature, the tracer will be in the fluid that is recovered Example—Oil and Gas Operations In the production of oil and gas from subterranean formations one must be knowledgeable about the formation. The present invention provides a system for releasing an active material into the subterranean formations for obtaining information about the formation or for acting on fluids in the formations or on the formations themselves. The present invention provides a capsule having a shell with an active material contained in the capsule inside the shell. The capsule having a shell and the active material contained in the capsule inside the shell is introduced into the formations. A triggering mechanism provides the release of the active material from said capsule into the formations. The microencapsulation of active material relies on the ability to contain the active material in a capsule, inject the capsule into the geologic formation as part of a desired test or action on the formations, and release the active material from the capsule. By preparing capsules of an appropriate material and wall thickness, the active material will be triggered for release when it comes into contact with fluids of the appropriate temperature, chemistry, or time. Other triggering mechanisms such as electromagnetic radiation and pressure pulsed can be used.

Referring again to FIG. 1, an active material 104 is encapsulated in a shell 102. The active material 104 can be a tracer material or a material that will act on the fluid in the formation or on the formation itself. The shell 102 can be made of different materials and different wall thicknesses to achieve the desired result.

Referring again to FIG. 4, the example of a tracer for oil and gas operations provides a system for releasing an active material into an underground formation of the present invention is illustrated by a flow chart. In the first step the capsule containing the active material is injected into the underground formation. In the next step the active material is released from the capsule in the underground formation upon encountering the pre-determined temperature. The trigger mechanism is activated to act on the shell of the capsule to release the active material into the underground formation.

In the final step the active material is recovered and analyzed or the results of the action are evaluated. For example fluid may be recovered at an extraction well. If an active tracer has been released by encountering the predetermined temperature, the active tracer will be in the fluid that is recovered. Tracers tests are a standard method for obtaining information about the interconnectedness of individual wells, pathways, sweep efficiency, reservoir storage volume, and the types of fluid at depth (through the use of tracers that have distinct distribution coefficients). The microencapsulated tracers of the present invention will enable the collection of valuable additional information such as temperature, pressure, and fluid composition.

Example—Latent Catalyst

The present invention provides system for releasing a material into an environment. The material may be encapsulated in a capsule or otherwise packaged for movement into the environment for release. The capsule includes a shell with the material inside the shell. The capsule is introduced into the environment. A triggering causes release of the material from the capsule into the environment. The material and a catalyst are encapsulated in the capsule. Activation of the catalyst is triggered to act on the shell to release the material. The triggering causes release of the material from the capsule into the environment. The system has many uses. For example, the system has use in geological applications, in the release of drugs and therapeutics in biological and medical applications, and in the delivery of other useful encapsulated materials where non-encapsulated delivery seems untenable.

Figure 5:
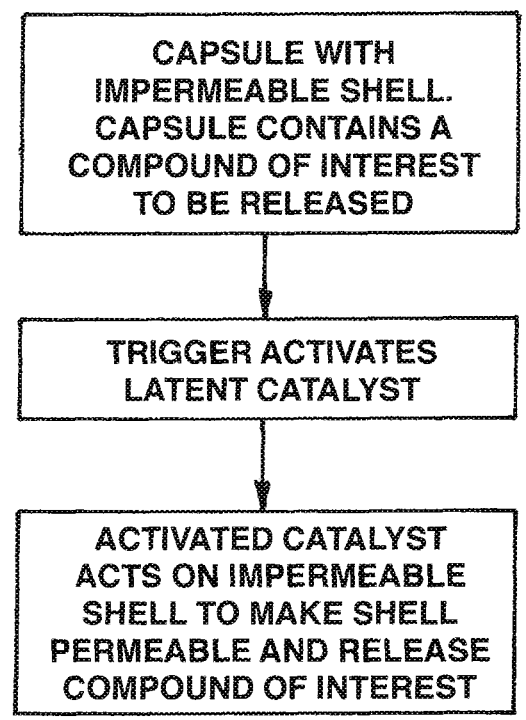
FIG. 5 is an illustration of another example of a system of the present invention.

Referring to FIG. 5, an example of system wherein a capsule contains a chemical compound and a latent catalyst. FIG. 5 is a flow chart illustrating the steps of system wherein a capsule contains a chemical compound and a latent catalyst.

As illustrated in FIG. 5, a capsule with an impermeable shell contains a chemical compound and a latent catalyst.

In the first step a capsule with a selectively impermeable shell and a latent catalyst is produced. The capsule contains a compound of interest to be released into the environment. The capsule is designed with a trigger system that will cause the shell to become permeable to the compound of interest and release it from the capsule by triggering the latent catalyst causing the latent catalyst to become active and act on the shell so the shell becomes permeable and release the compound of interest. For example, the shell may be comprised of a hydrophobic polymer such as the tertiary butyl carbonate of hydroxyl ethyl acrylate. The catalyst used can be a thermally generated acid, such as the ammonium salt of a strong acid or the tert-butyl carbonate of p-toluenesulfonic acid. Upon heating, the thermally activated acid catalytically converts the hydrophobic shell polymer into a hydrophilic polymer, in this case poly hydroxyethyl acrylate. This causes an increase in shell permeability, releasing the encapsulated material. The evolution of $CO_2$ may also degrade shell integrity and release the encapsulated material. The trigger for the catalyst can, for example, can be heat or light or other triggering mechanisms.

Example—Targeted Medication Delivery

In traditional drug delivery systems such as oral ingestion or intravascular injection, the medication is distributed throughout the body through the systemic blood circulation. Only a small portion of the medication reaches the organ to be affected.

Applicant's targeted drug delivery system concentrates the medication in the organ or tissue of interest while reducing the relative concentration of the medication in the remaining organs and tissue. By avoiding the patient's defense mechanisms and inhibiting non-specific distribution in the liver and spleen a better drug delivery system is provided. Targeted delivery is believed to improve efficacy while reducing side-effects.

Figure 6:
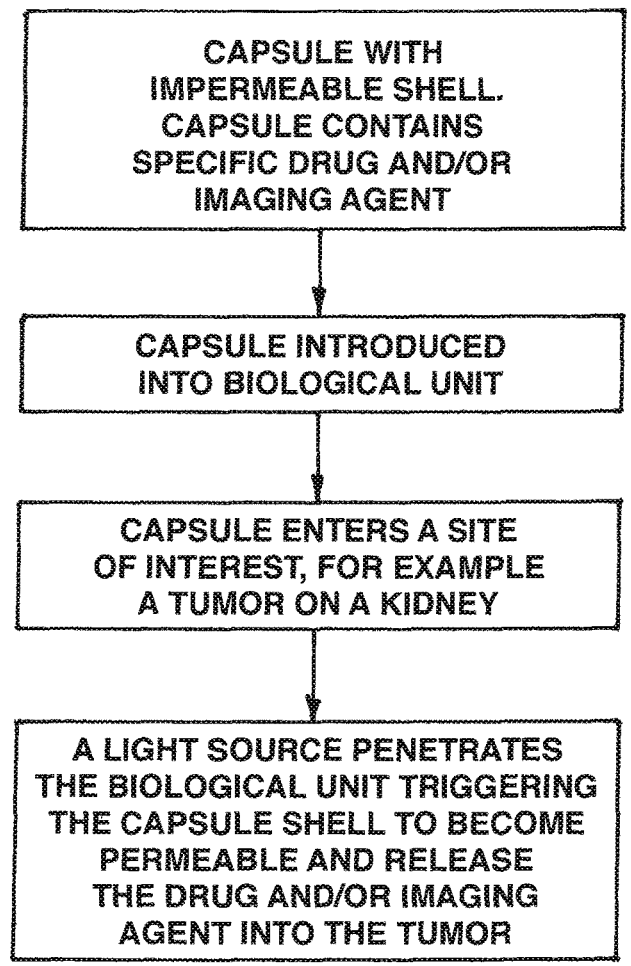
FIG. 6 is an illustration of yet another example of a system of the present invention.

One example of a targeted medication delivery system of the present invention is illustrated in FIG. 6. FIG. 6 is a flow chart illustrating a number of steps that result in the targeted medication delivery system of the present invention concentrating the medication in the organ or tissue of interest while reducing the relative concentration of the medication in the remaining organs and tissue. The targeted medication delivery system of the present invention delivers a certain amount of a therapeutic drug for a prolonged period of time to a targeted diseased area within the body. This helps maintain the required drug levels in the body' targeted diseased area, thereby preventing any damage to the healthy tissue and organs by the drug.

In the first step of Applicant's targeted drug delivery system a capsule with a selectively impermeable shell is produced. The capsule contains the specific drug for the organ or tissue of interest. The capsule is designed with a trigger system that will cause the shell to become permeable to the drug for the organ or tissue of interest and release the drug from the capsule.

In the next step of Applicant's targeted drug delivery system the capsule containing the specific drug introduced into the patient's body.

In the next step of Applicant's targeted drug delivery system the capsule containing the specific drug is directed to the organ or tissue of interest. The capsule enters a site of interest, for example a tumor on a kidney.

In the next step of Applicant's targeted drug delivery system the release of the drug is triggered. This is accomplished by using a source of light to penetrate the patient's tissue onto the capsule located in or on the organ or tissue of interest. The light triggers the capsule shell to become permeable and release the drug into the organ or tissue of interest, i.e. the tumor.

More specifically, the triggering the capsule shell to become permeable can be accomplished by constructing the capsule shell of a hydrophobic material that becomes hydrophilic upon exposure to light. For example, the shell can be hydrophobic poly (4,5-dimethoxy-2-nitrobenzyl acrylate), which is converted to hydrophilic poly acrylic acid upon exposure to light. In other embodiments the capsule is designed with a trigger system that will dissolve the shell or erode the shell and release the drug to the organ or tissue of interest.

Example—Latent Catalyst Targeted Drug Delivery

In traditional drug delivery systems such as oral ingestion or intravascular injection, the medication is distributed throughout the body through the systemic blood circulation. Only a small portion of the medication reaches the organ to be affected.

Applicant's latent catalyst targeted drug delivery system concentrates the medication in the organ or tissue of interest while reducing the relative concentration of the medication in the remaining organs and tissue. By avoiding the patient's defense mechanisms and inhibiting non-specific distribution in the liver and spleen a better drug delivery system is provided. Targeted delivery is believed to improve efficacy while reducing side-effects.

Figure 7:
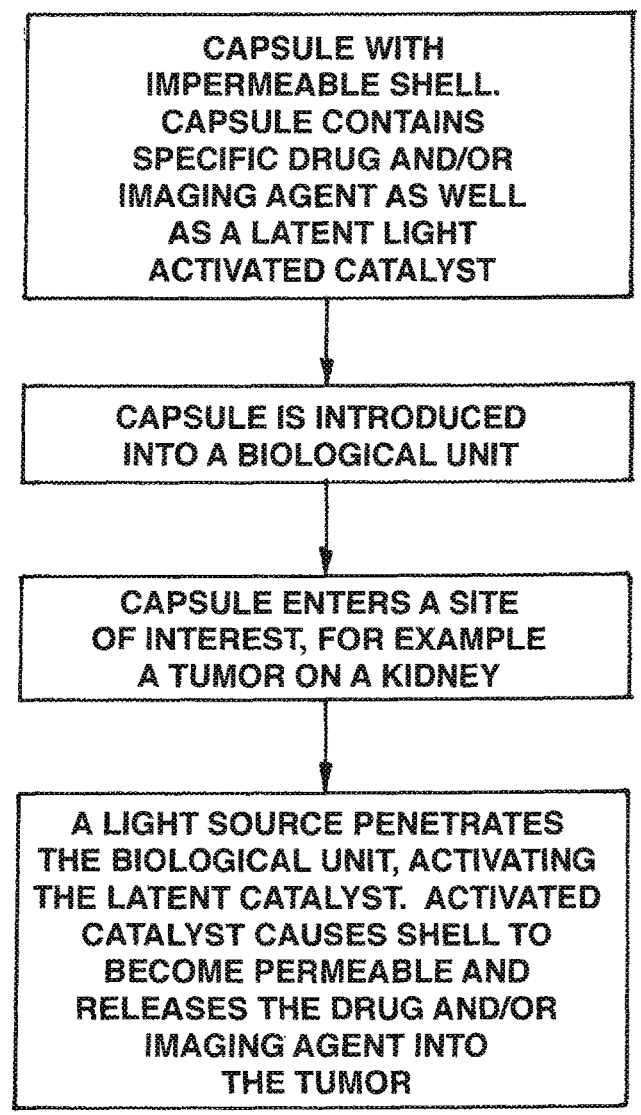
FIG. 7 is an illustration of one example of a system of the present invention.

An example of Applicant's latent catalyst targeted drug delivery system of the present invention is illustrated in FIG. 7. FIG. 7 is a flow chart illustrating a number of steps that result in the latent catalyst targeted drug delivery system of the present invention concentrating the medication in the organ or tissue of interest while reducing the relative concentration of the medication in the remaining organs and tissue. The targeted drug delivery system delivers a certain amount of a therapeutic drug for a prolonged period of time to a targeted diseased area within the body. This helps maintain the required drug levels in the body' targeted diseased area, thereby preventing any damage to the healthy tissue and organs by the drug.

In the first step of Applicant's latent catalyst targeted drug delivery system a capsule with a selectively impermeable shell and a latent light activated catalyst is produced. The capsule contains the specific drug for the organ or tissue of interest. The capsule is designed with a trigger system that will cause the shell to become permeable to the drug for the organ or tissue of interest and release the drug from the capsule by light acting on the latent catalyst causing the latent catalyst to become active and become permeable and release the drug.

In the next step of Applicant's latent catalyst targeted drug delivery system the capsule containing the specific drug introduced into the patient's body.

In the next step of Applicant's latent catalyst targeted drug delivery system the capsule containing the specific drug is directed to the organ or tissue of interest. The capsule enters a site of interest, for example a tumor on a kidney.

In the next step of Applicant's targeted drug delivery system the release of the drug is triggered. This is accomplished by using a source of light to penetrate the patient's tissue onto the capsule located in or on the organ or tissue of interest. The light triggers the latent catalyst to become active and the capsule shell to become permeable and release the drug into the organ or tissue of interest, i.e. the tumor.

More specifically, the triggering the latent catalyst to become active causing the capsule shell to become permeable can be accomplished by constructing the capsule of a hydrophobic polymer such as the tertiary butyl carbonate of hydroxyl ethyl acrylate. The catalyst used can be a thermally generated acid, such as the ammonium salt of a strong acid or the tert-butyl carbonate of p-toluenesulfonic acid. Upon heating, the thermally activated acid catalytically converts the hydrophobic shell polymer into a hydrophilic polymer, in this case poly hydroxyethyl acrylate. This causes an increase in shell permeability, releasing the encapsulated material. The evolution of $CO_2$ may also degrade shell integrity and release the encapsulated material. The trigger for the catalyst can, for example, can be heat or light or other triggering mechanisms. For example, the 4,5-dimethoxy-2-nitrobenzy ester of para-toluenesulfonic acid can be used as a photocatalyst to generate an acid to decompose the polymer mentioned above.

Example—Flash Grenade

Figure 8A:
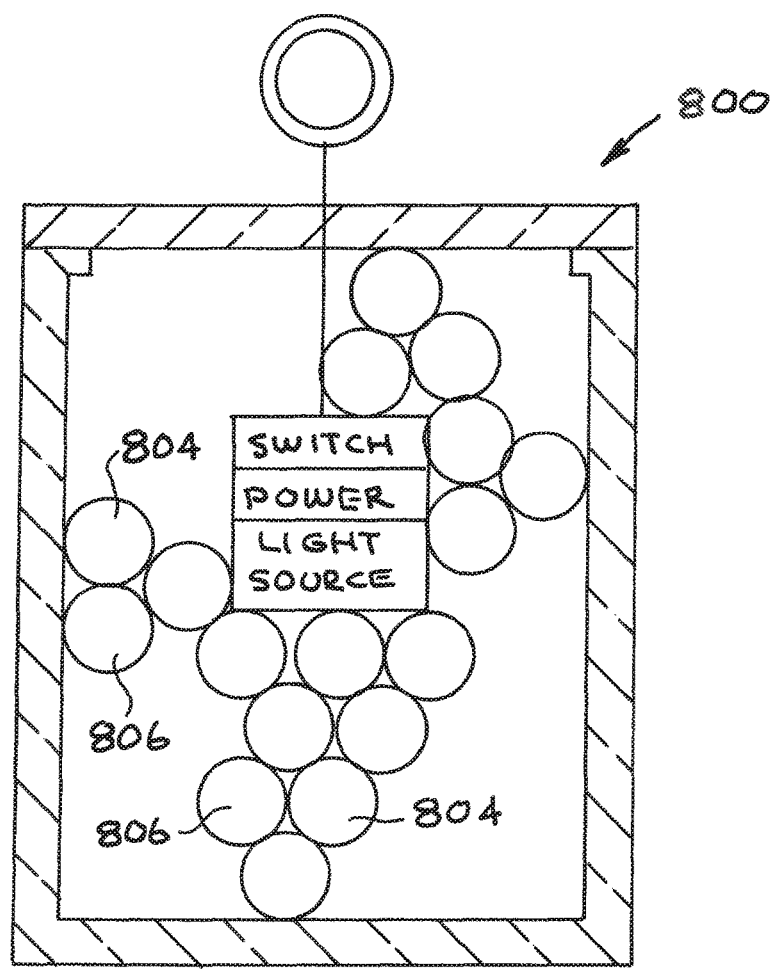
FIGS. 8A and 8B are illustrations of additional examples of systems of the present invention.
Figure 8B:
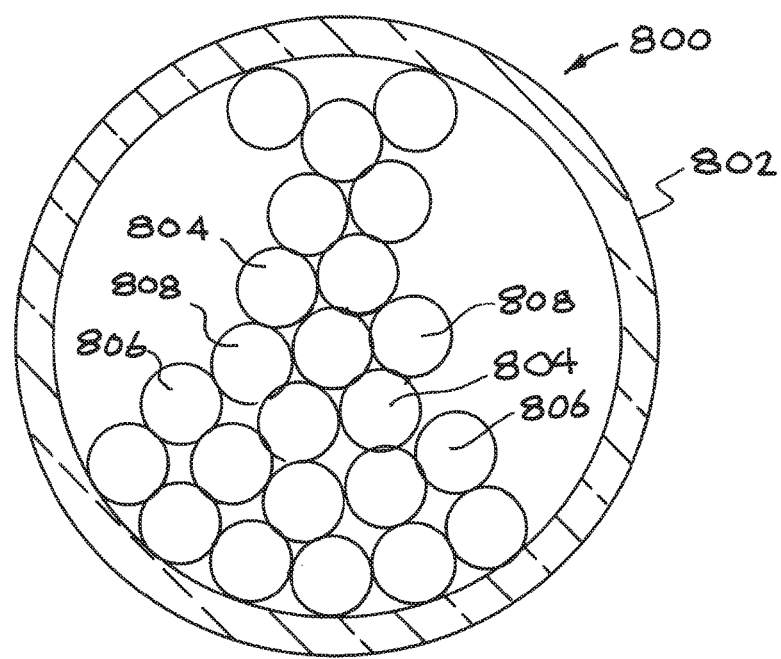

Referring to FIGS. 8A and 8B, examples of flash grenade are illustrated. The flash grenade is designated generally by the reference numeral 800. The flash grenade 800 includes a container or a canister 802. The container or canister 802 is filled with capsules 804, 806, and 808. The capsules 804, 806, and 808 have shells as described in the previous examples.

The capsules 804 contain a first reactive compound, such as oxygen. The capsules 806 contain a second reactive compound that reacts with the first reactive compound, such as material that reacts with oxygen.

The shells of the capsules 804, 806, and 808 prevent the compounds in the shells from reacting with the other compounds in the other shells. A trigger mechanism breaks the shells to release the compounds causing them to react.

In one embodiment the capsules 804 contain oxygen as the first reactive compound. The capsules 806 contain zirconium or some other reducing agent or fuel as the second reactive compound. The trigger mechanism is a small ultraviolet source such as a heated filament. This is illustrated by the unit identified as switch, power, and light source in FIG. 8A. The shells of the capsules 804 and 806 material are designed to decompose upon exposure to ultraviolet light. Because the reaction of oxygen from capsules 804 and zirconium from capsules 806 produces ultraviolet light, the reaction is self-sustaining. The shell material may be a variety of polymers sensitive to ultraviolet light, including for example Kevlar or other polyaromatics, poly 2-nitrobenzyl esters, acetals and carbonates, or polyacetals of photoinitiating compounds such as benzoin or avobenzone.

In another embodiment the capsules 804 contain oxygen as the first reactive compound and the capsules 806 contain zirconium or some other reducing agent or fuel as the second reactive compound. The breaking of the shells of the capsules 804 and 806 is triggered by a material in the capsules 808. For example acid is contained in capsules 808 and the shells of capsules 808 are breakable. The canister 802 is a flexible canister. When the flexible canister 802 lands al the target location the breakable shells of capsules 808 are broken releasing the acid to decompose the shells of the capsules 804 and 806.

Although the description above contains many details and specifics, these should not be construed as limiting the scope of the invention but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present invention fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A flash grenade apparatus for releasing a material into an environment, comprising:
   a capsule, said capsule having an exterior shell and an interior,
   an active material contained in said interior of said capsule, and
   a triggering mechanism for acting on the exterior shell of the capsule and releasing said active material from said interior of said capsule into the environment,
   wherein said triggering mechanism for acting on the exterior shell of the capsule and releasing said active material from said interior of said capsule into the environment is a latent catalyst that is triggered to become an active catalyst and act on the exterior shell of the capsule and releasing said active material from said interior of said capsule into the environment,
   wherein said latent catalyst that is triggered to become an active catalyst is a latent catalyst that is triggered by electromagnetic radiation, and
   wherein said active material contained in said interior of said capsule is a first reactive material and a second reactive material that reacts with said first reactive material for providing the flash grenade apparatus.

* * * * *